(12) United States Patent
Wheeler et al.

(10) Patent No.: US 7,049,425 B2
(45) Date of Patent: May 23, 2006

(54) METHODS AND COMPOSITIONS UTILIZING AN ALTERNATIVE SPLICE VARIANT OF THE SIGMA-1 RECEPTOR

(75) Inventors: Kenneth T. Wheeler, Winston-Salem, NC (US); Robert H. Mach, Winston-Salem, NC (US); Steven Childers, Winston-Salem, NC (US); Gregory Shelness, Winston-Salem, NC (US); Li-Ming Wang, Bethesda, MD (US)

(73) Assignee: Wake Forest University, Winston-Salem, NC (US)

( * ) Notice: Subject to any disclaimer, the term of this patent is extended or adjusted under 35 U.S.C. 154(b) by 435 days.

(21) Appl. No.: 09/823,069

(22) Filed: Mar. 30, 2001

(65) Prior Publication Data

US 2002/0061847 A1    May 23, 2002

Related U.S. Application Data

(60) Provisional application No. 60/193,694, filed on Mar. 31, 2000.

(51) Int. Cl.
*C07H 21/04* (2006.01)
*C12N 15/63* (2006.01)
*C12N 15/09* (2006.01)

(52) U.S. Cl. .................. 536/23.5; 435/69.1; 435/172.3; 435/235.1; 435/325; 435/320.1; 536/350

(58) Field of Classification Search .................. 435/7.1, 435/69.1, 252.3, 325; 530/300, 350; 536/23.1, 536/24.31
See application file for complete search history.

(56) References Cited

U.S. PATENT DOCUMENTS

| | | | |
|---|---|---|---|
| 4,709,094 A | 11/1987 | Weber et al. | 564/238 |
| 5,231,099 A | 7/1993 | Cook | 514/279 |
| 5,604,228 A | 2/1997 | Keana et al. | 514/255 |
| 5,753,516 A | 5/1998 | Heagy et al. | 436/501 |
| 5,863,766 A | 1/1999 | Hillman et al. | 435/69.1 |
| 5,866,323 A | 2/1999 | Markowitz et al. | 435/6 |
| 5,911,970 A | 6/1999 | John et al. | 424/1.85 |
| 5,916,755 A | 6/1999 | Kraus et al. | 435/7.1 |
| 5,919,934 A | 7/1999 | John et al. | 546/247 |

FOREIGN PATENT DOCUMENTS

WO    WO 97/34892    9/1997

OTHER PUBLICATIONS

Bowie et al, Dicphering the Message in Protein Pequences Tolerance to Amino Acid Substitutions, Mar. 16, 1990, Science, vol. 247, p. 1307-1010.*
Database Genback, Accession No. AF226604, Wang et al., *Homo sapiens sigma 1 receptor beta variant mRNA, complete cds, alternatively spliced; 100% identical to SEQ ID No.: 1, encoding a polypeptide comprising an amino acid sequence 100% identical to SEQ ID No.: 2*, Apr. 18, 2000.
International Search Report, PCT/US01/10650, Oct. 11, 2001.
I. Al-Nabulsl et al. Effect of ploidy, recruitment, enviromental factors, and tamoxifen treatment on the expression of sigma-2 receptors in proliferating and quiescent tumour cells. *British Journal of Cancer* 81, 925-933 (1999).
M.E. Ganapathy et al. Molecular and ligand-binding characterization of the sigma-receptor in the Jurkat human T lymphocyte cell line. *J Pharmacol Exp Ther* 289, 251-260 (1999).
R.H. Mach et al. Sigma 2 receptors as potential biomarkers of proliferation in breast cancer. *Cancer Res* 57, 156-161 (1997).
K.T. Wheeler et al. Sigma-2 receptors as a biomarker of proliferation in solid tumours. *Br J Cancer* 82, 1223-1232 (2000).

* cited by examiner

*Primary Examiner*—Joseph Murphy
*Assistant Examiner*—Nirmal S. Basi
(74) *Attorney, Agent, or Firm*—Myers Bigel Sibley & Sajovec PA

(57) ABSTRACT

A new variant of the sigma-1 ($\sigma_1$)receptor is useful in screening compounds useful in the imaging and treatment of proliferative masses (i.e., tumors). This new variant, named sigma—$_{1\beta}$ ($\sigma_{1\beta}$) finds particular use in the non-invasive diagnosis of cancer and more particularly in the diagnosis of proliferative cancer cells.

6 Claims, 7 Drawing Sheets

```
  1 ATGCAGTGGGCCGTGGGCCGGCGGTGGGCCGTGCTCCTGGCTGTCGCAGCG   60
    M  Q  W  A  V  G  R  R  W  A  A  L  L  L  A  V  A  A

61 GTGCTGACCCAGGTCGTCGTGTGGCTCTGGCTGGGTACGCAGAGCTTCGTCTTCCAGCGCGAA  120
    V  L  T  Q  V  V  V  W  L  W  L  G  T  Q  S  F  V  F  Q  R  E

121 GAGATAGCGCAGTTGGCCCGGCAGTACGCTGGGCTGGACCACGAGCTGGCCTTCTCTCGT  180
    E  I  A  Q  L  A  R  Q  Y  A  G  L  D  H  E  L  A  F  S  R

181 CTGATCGTGGAGCTGCGCGGCCTGCACCCAGGCCACGTGCTGCCGGACGAGGAGCTGCAG  240
    L  I  V  E  L  R  R  L  H  P  G  H  V  L  P  D  E  E  L  Q

241 TGGGTGTTCGTGAATGCGGGGTGGATGGGCGCCATGTGCCTTCTGCACGCCTCGCTG  300
    W  V  F  V  N  A  G  W  M  G  A  M  C  L  L  H  A  S  L

301 TCCGAGTATGTGCTGCTCTTCGGCACGGCCCTTGGGCTCCCCGGCCACTCGGGGGAGACG  360
    S  E  Y  V  L  L  F  G  T  A  L  G  S  R  G  H  S  G  E  T

361 GTAGTACACGGGCCCGGCGAGGCAATAGCTGTGGAGTGGGGCCAAACACATGGATGGTG  420
    V  V  H  G  P  G  E  A  T  A  V  E  W  G  P  N  T  W  M  V

421 GAGTACGGCCGGGGCGTCATCCCATCCACCCTGGCCTTCGCACTGGCCGACACTGTCTTC  480
    E  Y  G  R  G  V  I  P  S  T  L  A  F  A  L  A  D  T  V  F

481 AGCACCCAGGACTTCCTCACCACCTACCTCTTCTATACTCTTCGCTCCTATGCTCGGGGCCTCCGG  540
    S  T  Q  D  F  L  T  T  Y  L  F  Y  T  L  R  S  Y  A  R  G  L  R

541 CTTGAGCTCACCACCTACCTCTTTGGCCAGGACCCTTGA  579
    L  E  L  T  T  Y  L  F  G  Q  D  P  *
```

FIG. 2

```
  1   MQWAVGRRWAWAALLLAVAAVLTQVVWLWLGTQSFVFQREEIAQLARQYA              50
  1   MQWAVGRRWAWAALLLAVAAVLTQVVWLWLGTQSFVFQREEIAQLARQYA              50

51   GLDHELAFSRLIVELRRLHPGHVLPDEELQWVFVNAGGWMGAMCLLHASL             100
 51   GLDHELAFSRLIVELRRLHPGHVLPDEELQWVFVNAGGWMGAMCLLHASL             100

101   SEYVLLFGTALGSRGHSGRYWAEISDTIISGTFHQWREGTTKSEVFYPGE             150
101   SEYVLLFGTALGSRGHS(117)    [31 AA WERE DELETED]     GE         119

151   TVVHGPGEATAVEWGPNTWMVEYGRGVIPSTLAFALADTVFSTQDFLTLF             200
120   TVVHGPGEATAVEWGPNTWMVEYGRGVIPSTLAFALADTVFSTQDFLTLF             169

201   YTLRSYARGLRLELTTYLFGQDP      223 AA   HUMAN σ₁  RECEPTOR PROTEIN
170   YTLRSYARGLRLELTTYLFGQDP      192 AA   HUMAN σ₁ᵦ RECEPTOR PROTEIN
```

FIG. 3

```
  1 ATGCCGTGGGCCGCGGGACGGGCGGTGGGCCATGGATCACCCTGATTCTGACTATTATCGCA   60
    M  P  W  A  A  G  R  R  R  W  A  W  I  T  L  I  L  T  I  I  A

61 GTGCTGATCCAGGCCGCCTGGTTGTGGCTGGGCACTCAAAACTTCGTCTTCTCTAGAGAA  120
    V  L  I  Q  A  A  W  L  W  L  G  T  Q  N  F  V  F  S  R  E

121 GAAATAGCGCAGCTTGCTCGACAGTATGCGGGGCTGGACCATGAGCTTGCCTTCTCTCGG  180
    E  I  A  Q  L  A  R  Q  Y  A  G  L  D  H  E  L  A  F  S  R

181 CTGATCGTGGAGCTGCGCCGGAGCTGCACCGTGCTGCCGGATGAGGAGCTGCAG  240
    L  I  V  E  L  R  R  L  H  P  G  H  V  L  P  D  E  E  L  Q

241 TGGGTATTTGTGAACGCGGGGTGGATGGGCGCCATGTGTATTCTGCACGCCTCGCTG  300
    W  V  F  V  N  A  G  G  W  M  G  A  M  C  I  L  H  A  S  L

301 TCTGAGTACGTGCTGCTCTTCGGCACCGCCCTGGGCTCCCATGGCCATTCGGGAGAGACA  360
    S  E  Y  V  L  F  G  T  A  L  G  S  H  G  H  S  G  E  T

361 GTTGTACACGGGCCTGGAGAAGCAACGGCTCTGGAGTGGGGACCAAACACGTGGATGGTG  420
    V  V  H  G  P  G  E  A  T  A  L  E  W  G  P  N  T  W  M  V

421 GAGTACGGCCGGGGTGTTATTCCGTCTACCCTGTTCTTTGCACTAGCCGACACCTTCTTC  480
    E  Y  G  R  G  V  I  P  S  T  L  F  F  A  L  A  D  T  F  F

481 GGCACCCAGGACTACCTCACACTCTTCTATACCCTTCGGGCCTATGCCCGGGCCCTCCGG  540
    G  T  Q  D  Y  L  T  L  F  Y  T  L  R  A  Y  A  R  G  L  R

541 CTTGAGCTTACCACCTACCTCTTTGGCCAAGACTCCTGA  579
    L  E  L  T  T  Y  L  F  G  Q  D  S  *
```

FIG. 4

```
1    MPWAAGRRWAWITLILTIIAVLIQAAWLWLGTQNFVFSREEIAQLARQYA    50
1    MPWAAGRRWAWITLILTIIAVLIQAAWLWLGTQNFVFSREEIAQLARQYA    50

51   GLDHELAFSRLIVELRRLHPGHVLPDEELQWVFVNAGGWMGAMCILHASL    100
51   GLDHELAFSRLIVELRRLHPGHVLPDEELQWVFVNAGGWMGAMCILHASL    100

101  SEYVLLFGTALGSHGHSGRYWAEISDTIISGTFHQWKEGTTKSEVFYPGE    150
101  SEYVLLFGTALGSHGHS  (117)         GE                 119
                         [31 AA WERE DELETED]

151  TVVHGPGEATALEWGPNTWMVEYGRGVIPSTLFFALADTFFGTQDYLTLF    200
120  TVVHGPGEATALEWGPNTWMVEYGRGVIPSTLFFALADTFFGTQDYLTLF    169

201  YTLRAYARGLRLELTTYLFGQDS*  223 AA    σ₁   RECEPTOR PROTEIN
170  YTLRAYARGLRLELTTYLFGQDS*  192 AA    σ₁ᵦ  RECEPTOR PROTEIN
```

FIG. 5

METHODS AND COMPOSITIONS UTILIZING AN ALTERNATIVE SPLICE VARIANT OF THE SIGMA-1 RECEPTOR

RELATED APPLICATIONS

This application claims the benefit of U.S. Provisional Application No. 60/193,694, filed Mar. 31, 2000, which is incorporated herein in its entirety.

FIELD OF THE INVENTION

This invention relates to a new variant of the sigma-1 ($\sigma_1$) receptor and methods and compositions utilizing the same.

BACKGROUND OF THE INVENTION

A significant problem in the clinical management of cancer is the identification of an appropriate treatment strategy. For example, the choice of whether a patient is subjected to conventional versus fractionated radiation therapy is often dependent upon the proliferative status of a tumor. The primary measure of proliferative status is the determination of the S-phase fraction of a tumor. This is traditionally determined by flow cytometric measurements of tissue biopsy samples. Patients with tumors exhibiting a high S-phase fraction display a greater likelihood of tumor recurrence and have a higher death rate. These patients, who are predicted to have a poor response to conventional radiation therapy, are often chosen for an accelerated radiation fractionation schedule.

Although S-phase fraction is an objective method for measuring the proliferative status of tumors, there are a number of complications that limit the accuracy of the procedure. For example, in breast cancer, 30–40% of biopsy samples cannot be evaluated by flow cytometric analysis. Furthermore, tissue sampling by biopsy can be problematic since most tumors are heterogeneous, and consist of both proliferative and nonproliferative cells. Therefore, tissue samples obtained from a tumor biopsy may not be representative of the entire tumor cell population.

Imaging procedures that avoid many of the problems associated with traditional procedures include single photon emission computed tomography (SPECT) and positron emission tomography (PET). Unlike flow cytometry of biopsy samples, which sample only a fraction of the tumor, SPECT and PET can image and provide information about an entire tumor.

These imaging techniques have been used in conjunction with radioactive tracer compounds (radiotracers) that possess a high affinity for a protein having abnormal expression in tumor cells. The most prominent example of this approach is the use of radiolabeled monoclonal antibodies possessing a high affinity for tumor-radiolabeled monoclonal antibodies possessing a high affinity for tumor-associated antigens. Although some success has been obtained in this area, a number of complications, including heterogeneity of antigen-containing tumor cells, low tumor uptake, nonspecific radiotracer uptake in adjacent or other nontumor tissues, the presence of circulating antigens that compete with tumor cells for antibody, and the potential immunogenicity of the monoclonal antibody, have limited the general utility of this approach.

Another alternate approach for imaging tumors is the use of radiolabeled small molecules that possess a high affinity for receptors, such as sigma receptors, that are abnormally expressed in tumor cells. Sigma ($\sigma$) receptors have been defined as nonopiate, nondopaminergic, and nonphencyclidine receptors based on their ligand binding characteristics. It is believed that sigma receptors exist in at least two distinct subtypes, referred to as sigma-1 ($\sigma_1$) and sigma-2 ($\sigma_2$). An alternatively spliced variant of the $\sigma_1$ receptor, termed σ-R1A, has been cloned and expressed from Jurkat human T lymphocytes. M. E. Ganapathy et al. (*J. Pharmacol. Exp. Therap.* 289, 251 (1999). When compared to the $\sigma_1$ gene, this variant has three amino acid (AA) substitutions, a deletion in exon III (AA 118–149) and a loss of $\sigma_1$ ligand binding activity.

A high density of both sigma-1 and sigma-2 receptor subtypes have been expressed in many human and rodent tumor cell lines. See B. J. Vilner, et al., *Cancer Res.* 55:408–413 (1995). High levels of sigma receptors have also been reported in human tumor cells and in membrane preparations obtained therefrom. See, e.g., G. E. Thomas, *Life Sci.* 46:1279–1286 (1990); W. T. Bem, et al., *Cancer Res.* 51: 6558–6562 (1991); C. S. John, et al., *J. Nucl. Med.* 37:267P (1996); C. S. John, et al., *J. Nuc. Med.* 34:2169–2175 (1993); C. S. John, et al., *J. Med. Chem.* 37:1737–1739 (1994); C. S. John, et al., *Life Sci.* 56:2385–2392 (1995); C. S. John, et al., *J. Nucl. Med.* 37:205P (1996). Exemplary tumor cells and cell membranes expressing sigma receptors include brain tumor cells, breast tumor cells, human melanoma cells, non-small cell lung carcinoma cells, and human prostate tumor cells.

U.S. Pat. No. 5,863,766 to Hillman et al, describes the DNA sequence of a human sigma receptor, as well as isolated proteins encoded by the same and expression vectors, host cells, agonists, antibodies and antagonists of the same. U.S. Pat. Nos. 5,919,934 and 5,911,970 to John et al. describe compounds, methods and methods for cancer diagnosis, imaging and therapy, particularly in relation to cancer cells that have a cell surface sigma receptor.

Studies have suggested that $\sigma_2$ receptors are a biomarker of tumor cell proliferation. See e.g., Mach et al. *Cancer Research* 57, 156–161 (1997) and Al-Nabulsi et al., *British J. Cancer* 81, 925–933 (1999). Particularly, $\sigma_2$ receptors were found to be expressed eight to ten times more in proliferative (P) tumor cells than in quiescent (Q) tumor cells. In a recent study, the $\sigma_2$ receptor P:Q ratio was about 10.6 in solid tumors and about 9.5 in a tissue culture study. Wheeler et al., *Br. J. Cancer* 86, 1223–1234 (2000).

In view of the foregoing, sigma receptors are useful as markers in the non-invasive detection and visualization of a wide variety of tumors using single photon emission computed tomography and positron emission tomography technology. Previous reports have demonstrated that sigma receptors may serve as a target for radiotracers that can be used to anatomically image solid tumors. A correlation between sigma receptor density and the proliferative status of tumor cells was suggested in International Patent Application PCTUS97/04403 (claiming priority from U.S. Provisional Application 60/013,717, which is incorporated herein in its entirety). This application describes the discovery that $\sigma_2$ receptor density correlates with the proliferative status of breast tumor cells, and also describes a non-invasive method to detect cancer cells or to assess the proliferative status of cancer cells which express $\sigma_2$ receptors, using detectably labeled $\sigma_2$ ligands. International Application PCT/US00/13834 (claiming priority from U.S. Provisional Application 60/135,274, which is incorporated herein in its entirety), describes methods of determining the proliferative status of cancer cells by determining the ability of proliferative cells to bind $\sigma_1$ and $\sigma_2$ ligands, respectively. Specifically, it is suggested that the ratio of $\sigma_2$ to $\sigma_1$ density on a cell is an indicator of the proliferative state of the cell. See also Wheeler et al., supra, which is also incorporated herein by reference.

Despite the reported use of detectably labeled $\sigma_2$ ligands to determine the proliferative status of cancer cells, there remains a need for additional methods and compositions for accurately assessing the proliferative status of cancer cells. A need also remains for non-invasive methods and compositions that are useful for imaging tumors and diagnosing cancer and other disorders of cell proliferation.

SUMMARY OF THE INVENTION

The present invention is based on the characteristics of a newly discovered variant of the $\sigma_1$ receptor. The variant was cloned from mouse mammary adenocarcinoma cells and human breast tumor cells. When compared to the $\sigma_1$ receptor, the variant exhibits a deletion in Exon III (AA 117–148) of $\sigma_1$, but no amino acid substitutions. The new variant is referred to herein as sigma-$_{1\beta}$ ($\sigma_{1\beta}$). When $\sigma_{1\beta}$ is expressed in COS-cells, there is a slight increase (about 1.2 fold) in $\sigma_1$-like binding, but a substantial increase (about four-fold) in $\sigma_2$-like binding, as compared with cells not expressing the receptor. Because this new variant exhibits $\sigma_2$-like binding, it is useful in the screening of compounds useful in the detection of the proliferation state of tumors, as well as in other uses. The new $\sigma_{1\beta}$ variant finds particular use in the non-invasive diagnosis of cancer and more particularly in the diagnosis of proliferative cancer cells.

Accordingly, the invention provides isolated polynucleotide sequences encoding the human and rodent $\sigma_{1\beta}$ receptors. The polynucleotide sequence may be selected from the group consisting of:

(a) polynucleotides having the nucleotide sequence given herein as SEQ ID NO:1 (which encodes the protein having the amino acid sequence given herein as SEQ ID NO:2);

(b) polynucleotides having the nucleotide sequence given herein as SEQ ID NO:3 (which encodes the protein having the amino acid sequence given herein as SEQ ID NO:4);

(c) polynucleotides that hybridize to polynucleotides of (a) or (b) above (e.g., under stringent conditions) and which encode a $\sigma_{1B}$ receptor; and (d) polynucleotides that differ from the polynucleotides of (a) or (b) above due to the degeneracy of the genetic code, and which encode the $\sigma_{1\beta}$ receptor encoded by a polynucleotide of (a) or (b) above.

The present invention further provides an expression vector containing at least a fragment of any of the claimed polynucleotides sequences. In yet another aspect, the expression vector containing the polynucleotide sequence is contained within a host cell.

The invention further provides an isolated protein or fragment thereof encoded by a polynucleotide as given above (e.g., the proteins provided herein as SEQ ID NO: 2 or SEQ ID NO: 4).

The invention also relates to methods of determining whether candidate compounds are ligands of the $\sigma_{1\beta}$ receptor. In other words, certain embodiments of the present invention relate to screening candidate compounds for their ability to specifically bind to the $\sigma_{1\beta}$ receptor. When labeled, such compounds find use as diagnostic compounds for the imagining of, for example, tumor cells. These compounds also find use as therapeutics for the treatment of cancer and other disorders of cell proliferation. These ligand compounds are also useful in methods of determining the proliferative status of a tumor.

In carrying out methods of screening compounds for the ability to bind $\sigma_{1\beta}$, it is useful to have a source of isolated $\sigma_{1\beta}$ or polynucleotides encoding the same. Accordingly, certain embodiments of the invention relate to method for producing a polypeptide comprising the amino acid sequence of SEQ ID NO:2, or a fragment thereof, or an amino acid sequence of SEQ ID NO:4 or a fragment thereof. One embodiment of the method comprises the steps of: a) culturing a host cell containing an expression vector containing at least a fragment of the polynucleotide sequence encoding the $\sigma_{1\beta}$ under conditions suitable for the expression of the polypeptide; and b) recovering the polypeptide from the host cell culture.

Other embodiments of the invention relate to methods of imaging cells expressing the $\sigma_{1\beta}$ receptor. Still other embodiments relate to methods of determining the proliferative state of a cell. The density of $\sigma_{1\beta}$ in a cell can be determined by measuring the ability of the cell to bind ligands to the $\sigma_{1\beta}$ receptor. The density of the $\sigma_{1\beta}$ receptor may also be determined by measuring the "$\sigma_2$-like" binding of the sigma receptors on the cell. Although the $\sigma_{1\beta}$ receptor is present in normal cells, the overexpression of the receptor may indicate that the cell has become proliferative. If a cell loses its $\sigma_1$ activity but exhibits an increase in $\sigma_{1\beta}$ activity, the cell may have become proliferative. $\sigma_{1\beta}$-selective compounds, if able to be detected or imaged, may provide a means for detection of these cells. Alternatively, a measure of the ratio of $\sigma_{1\beta}$ to $\sigma_1$ binding of a cell may also provide an indication of the proliferative state of the cell. In a full grown tumor, or in a pre-cancerous lesion, if a cell has lost $\sigma_1$ activity but gained $\sigma_2$ activity, it may be an indication that the cells are proliferative. Accordingly, these methods may be used for monitoring recurrences of cancer, for identifying pre-cancerous lesions by proliferative status, or even for diagnosing cancer.

Another embodiment of the invention provides a pharmaceutical composition comprising a detectably labeled $\sigma_{1\beta}$ ligand, in a pharmaceutically acceptable carrier.

Still another embodiment of the invention provides a method for treating (i.e., inhibiting the growth of) cancer cells that express $\sigma_{1\beta}$ receptors comprising administering to a subject in need of such treatment an effective inhibitory amount of a $\sigma_{1\beta}$ ligand labeled with a therapeutic radionuclide (e.g., Rhenium-186 or Yttrium-90), or a pharmaceutically acceptable salt thereof.

The foregoing and other aspects of the present invention are explained in detail in the specification set forth below.

BRIEF DESCRIPTION OF THE DRAWINGS

FIG. 2 sets forth the mRNA (cDNA) [SEQ ID NO:1] and amino acid sequences [SEQ ID NO:2] of the human $\sigma_{1\beta}$ receptor (cd region). The mRNA sequence has GenBank accession number AF226604.

FIG. 3 is a comparison of the human $\sigma_1$ (SEQ ID NO:7) and $\sigma_{1\beta}$ (SEQ ID NO:2) receptor protein sequences.

FIG. 4 sets forth the mRNA (cDNA) [SEQ ID NO:3] and amino acid sequences [SEQ ID NO:4] of the mouse $\sigma_{1\beta}$ receptor (cd region). This sequence has GenBank accession number AF226605

FIG. 5 is a comparison of the mouse $\sigma_1$ (SEQ ID NO:8) and $\sigma_{1\beta}$ (SEQ ID NO:4) receptor protein sequences.

FIG. 6A illustrates the gel run on RT-PCR compounds, using $\sigma_1$ specific primers. FIG. 6B illustrates the gel run on RT-PCR compounds, using $\sigma_{1\beta}$ specific primers. M indicates DNA size markers (length of product indicated to left of gels in number of base pairs); Lane 1 is product located in brain; Lane 2 is product located in heart; Lane 3 is product located in lung; Lane 4 is product located in spleen; Lane 5 is product located in kidney; Lane 6 is product located in liver; Lane 7 is product located in intestine.

DETAILED DESCRIPTION OF THE PREFERRED EMBODIMENTS

Figure 1:
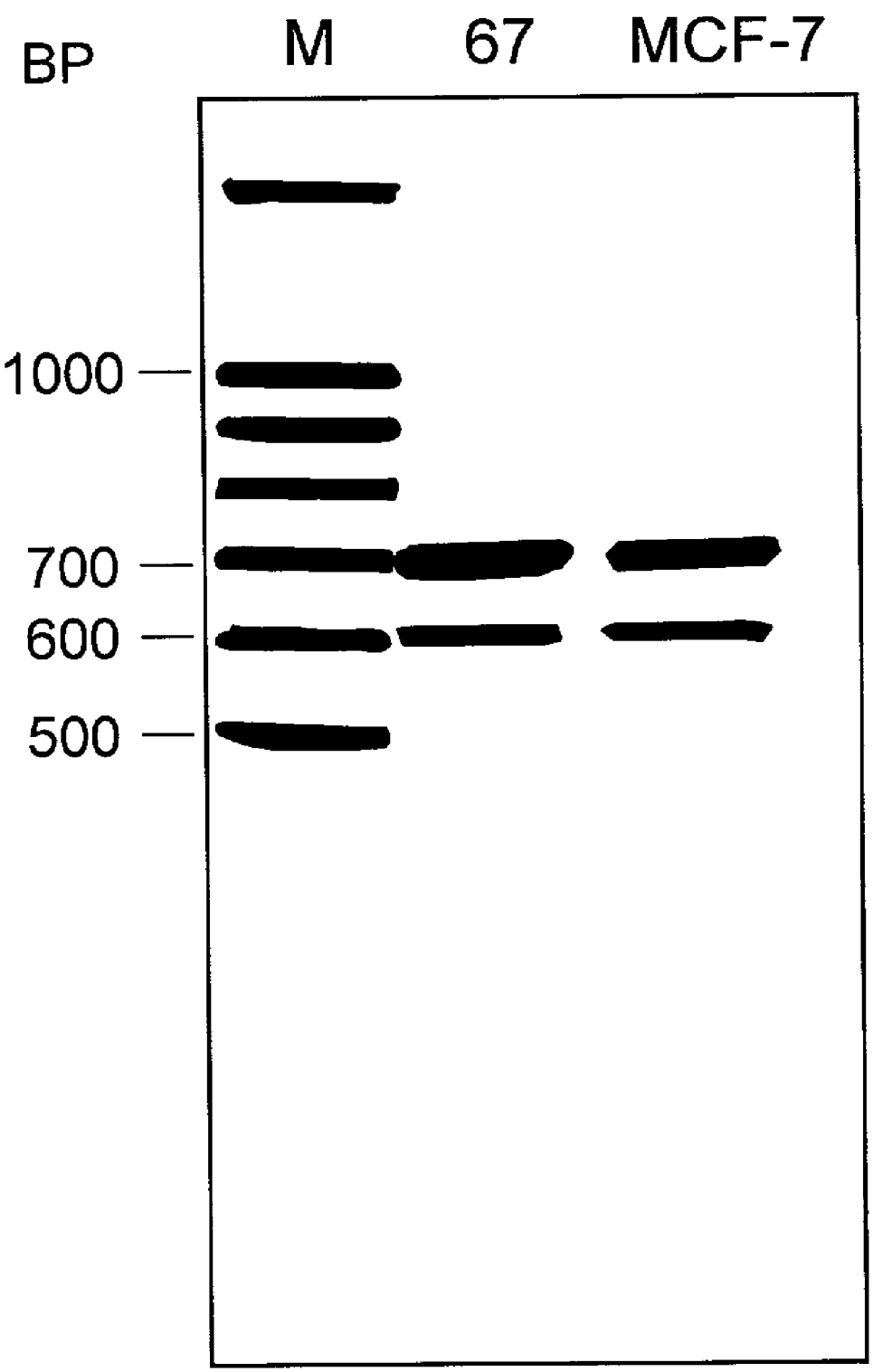
FIG. 1 is a photographic image of a gel illustrating the RT-PCR products from mouse and human breast tumor cells. Lane 1, labeled M (markers); Lane 2, labeled 67 (product in mouse cells); Lane 3 MCF-7 (product in human cells). Bands are measured in terms of number of base pairs (indicated to the left of the photograph).

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in accordance with standard usage. Amino acids are represented by three-letter code, in accordance with 37 CFR §1.822 and established usage. Alternatively, amino acids are represented by the one letter code commonly used by those skilled in the art as follows:

| Amino Acid | One Letter Code | Three Letter Code |
| --- | --- | --- |
| Alanine | A | Ala |
| Arginine | R | Arg |
| Asparagine | N | Asn |
| Aspartic Acid | D | Asp |
| Cysteine | C | Cys |
| Glutamic Acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |

-continued

| Amino Acid | One Letter Code | Three Letter Code |
| --- | --- | --- |
| Tryptophan | W | Trp |
| Tyrosine | Y | Tyr |
| Valine | V | Val |

The present application uses the terms "cancer" and "tumor" throughout. As used herein, the term "cancer" has its understood meaning in the art, for example, an uncontrolled growth of tissue that has the potential to spread to distant sites of the body (i.e., metastasize). Cancers of any origin, either tumor-forming or non-tumor forming cancers (although preferred embodiments of the invention relate to tumor-forming cancers). As used herein, the term "cancer cell" is also intended to encompass those cells referred to as "pre-cancerous," i.e., cells that contain mutated or damaged DNA or other components, which mutations or damage are likely to cause the cell to develop into a cancer cell. Exemplary cancers include osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; breast cancers; kidney cancers; endocrine cancers; skin cancers; melanomas; angiomas; and brain or central nervous system (CNS) cancers. Tumors or cancers, as defined herein, may be any tumor or cancer, primary or secondary. Preferred embodiments are methods of treating and preventing tumor-forming cancers. More preferred embodiments of the invention relate to brain and breast tumor cancers.

The term "tumor" is also understood in the art, for example, as an abnormal mass of cells within a multicellular organism. Generally, the growth of the abnormal cells of the tumor exceeds and is uncoordinated with that of normal cells. Furthermore, the abnormal growth of tumor cells generally persists in an abnormal (i.e., excessive) manner after the cessation of stimuli that originally caused the abnormality in the growth of the cells. Tumors can be malignant or benign. Preferably, the inventive methods disclosed herein are used to diagnose and treat malignant tumors.

The methods and compositions of the present invention are also useful in relation to non-cancer disorders of cell proliferation. These diseases include, but are not limited to, benign tumors, hyperplasias, hyperpigmentation of the skin, psoriasis, and any other disorder wherein cell proliferation is uncontrolled, and control, diagnosis, or imaging of such proliferation is desired.

The present invention relates to a new splice variant of the sigma receptor, which is referred to herein interchangeably as "$\sigma_{1\beta}$," or "$\sigma_{1\beta}$ receptor," or "$\sigma_{1\beta}$ protein." The mouse and human mRNA and amino acid sequences (cd region) of $\sigma_{1\beta}$ have been determined. SEQ ID NO:1 is the human mRNA (cDNA) sequence of $\sigma_{1\beta}$, and SEQ ID NO:2 is the human $\sigma_{1\beta}$ amino acid sequence. SEQ ID NO:3 is the mouse mRNA (cDNA) $\sigma_{1\beta}$ sequence, and SEQ ID NO:4 is the mouse of $\sigma_{1\beta}$ amino acid sequence. Accordingly, one aspect of the invention is isolated DNA encoding the human $\sigma_{1\beta}$ receptor. Another aspect is isolated DNA encoding rodent $\sigma_{1\beta}$ receptor. The present invention also encompasses isolated human $\sigma_{1\beta}$ protein and isolated rodent (mouse) $\sigma_{1\beta}$ protein. Such proteins may be isolated and/or purified in accordance with known techniques.

"Protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homophenylalanine, citrulline and noreleucine are considered amino acids for the purposes of the invention. "Amino acid" also includes imino acid residues such as proline and hydroxyproline. The side chains may be in either the (R) or the (S) configuration.

"Nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and O-methylphophoroamidite linkages, and peptide nucleic acid backbones and linkages. These alternative backbones are known in the art. Nucleic acids may be naturally occurring or synthetic or a combination. The nucleic acids may be single-stranded or double-stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

Polynucleotides of the present invention include those coding for proteins homologous to, and having essentially the same biological properties as, the proteins disclosed herein, and particularly the DNA disclosed herein as SEQ ID NO:1 and encoding the protein $\sigma_{1\beta}$ given herein SEQ ID NO:2; as well as the DNA disclosed herein as SEQ ID NO:3 and encoding the protein $\sigma_{1\beta}$ given herein as SEQ ID NO:4. This definition is intended to encompass natural allelic sequences thereof. Thus, isolated DNA or cloned genes of the present invention can be of any species of origin, including rodent (e.g., mouse, rat), rabbit, cat, porcine, and human, but are preferably of mammalian origin, more preferably of rodent origin, and most preferably of human origin. Thus, polynucleotides that hybridize to DNA disclosed herein as SEQ ID NO:1 (or fragments or derivatives thereof which serve as hybridization probes as discussed below) and which code on expression for a protein of the present invention (e.g., a protein according to SEQ ID NO:2); and polynucleotides that hybridize to DNA disclosed herein as SEQ ID NO:3 (or fragments or derivatives thereof which serve as hybridization probes as discussed below) and which code on expression for a protein of the present invention (e.g., a protein according to SEQ ID NO:4), are also an aspect of the invention.

Conditions which will permit other polynucleotides that code on expression for a protein of the present invention to hybridize to the DNA of SEQ ID NO:1 or SEQ ID NO: 3 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5× Denhardt's solution, 0.5% SDS and 1×SSPE at 37° C.; conditions represented by a wash stringency of 40–45% Formamide with 5× Denhardt's solution, 0.5% SDS, and 1×SSPE at 42° C.; and conditions represented by a wash stringency of 50% Formamide with 5× Denhardt's solution, 0.5% SDS and 1×SSPE at 42° C., respectively) to DNA of SEQ ID NO:1 or SEQ ID NO: 3 disclosed herein in a standard hybridization assay. See, e.g., J. Sambrook et al., *Molecular Cloning, A Laboratory Manual* (2d Ed. 1989) (Cold Spring Harbor Laboratory). In general, sequences which code for proteins of the present invention and which hybridize to the DNA of SEQ ID NO:1 or SEQ ID NO: 3 disclosed herein will be at least 75% homologous, 85% homologous, and even 95% homologous or more with SEQ ID NO:1 or SEQ ID NO:3, respectively. Further, polynucleotides that code for proteins of the present invention, or polynucleotides that hybridize to that as SEQ ID NO:1 or SEQ ID NO:3, but which differ in codon sequence from SEQ ID NO:1 or SEQ ID NO:3 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

Although nucleotide sequences which encode $\sigma_{1\beta}$ receptors are preferably capable of hybridizing to the nucleotide sequence of the naturally occurring $\sigma_{1\beta}$ under appropriately selected conditions of stringency, it may be advantageous to produce nucleotide sequences encoding $\sigma_{1\beta}$ or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding $\sigma_{1\beta}$ and its derivatives without altering the encoded amino acid sequences include the production of RNA transcripts having more desirable properties, such as a greater half-life, than transcripts produced from the naturally occurring sequence.

In one embodiment of the invention, $\sigma_{1\beta}$ nucleic acids (defined as polynucleotides encoding $\sigma_{1\beta}$ proteins or fragments thereof), or $\sigma_{1\beta}$ proteins (as defined above) are initially identified by substantial nucleic acid and/or amino acid sequence identity or similarity to the sequence(s) provided herein. In a preferred embodiment, $\sigma_{1\beta}$ nucleic acids or $\sigma_{1\beta}$ proteins have sequence identity or similarity to the sequences provided herein as described below and one or more of the $\sigma_{1\beta}$ protein bioactivities as further described herein. Such sequence identity or similarity can be based upon the overall nucleic acid or amino acid sequence.

As is known in the art, a number of different programs can be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387–395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351–360 (1987); the method is similar to that described by Higgins & Sharp *CABIOS* 5, 151–153 (1989).

Another example of a useful algorithm is the BLAST algorithm, described in Altschul et al., *J. Mol. Biol.* 215, 403–410, (1990) and Karlin et al., *Proc. Natl. Acad. Sci. USA* 90, 5873–5787 (1993). A particularly useful BLAST program is the WU-BLAST-2 program from Altschul et al., *Methods in Enzymology,* 266, 460–480 (1996). WU-BLAST-2 uses several search parameters, most of which are set to the default values.

The invention also encompasses production of polynucleotide sequences, or fragments thereof, which encode $\sigma_{1\beta}$, entirely by synthetic chemistry. After production, the synthetic sequence may be inserted into any of the many available expression vectors and cell systems using reagents that are well known in the art. Moreover, synthetic chemistry may be used to introduce mutations into a sequence encoding $\sigma_{1\beta}$ or any fragment thereof.

Knowledge of the nucleotide sequence as disclosed herein in SEQ ID NO:1 or SEQ ID NO:3 can be used to generate hybridization probes which specifically bind to the DNA of the present invention or to mRNA to determine the presence of amplification or overexpression of the proteins of the present invention.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. (Applicant specifically intends that the disclosure of all patent references cited herein be incorporated herein in their entirety by reference).

Methods for DNA sequencing which are well known and generally available in the art may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding $\sigma_{1\beta}$ may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) *PCR Methods Applic.* 2, 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins of the present invention need not express protein.

Suitable host cells include prokaryotes, yeast cells, or higher eukaryotic organism cells. Prokaryote host cells include gram negative or gram positive organisms, for example *Escherichia coli* (*E. coli*) or *Bacilli*. Higher eukaryotic cells include established cell lines of mammalian origin as described below.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or anautonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No.44076 or PEP4-1 (Jones, *Genetics* 85, 12 (1977). The presence of the trp1 lesion in the yeast host cell genome then provides an effective environment for detecting transformation by growth in the absence of tryptophan.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS, CV, and MDCK cell lines, with COS cells being preferred. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured Spodoptera frugiperda cells) and expression vectors such as the baculorivus expression vector (e.g., vectors derived from Autographa californica MNPV, Trichoplusia ni MNPV, Rachiplusia ou MNPV, or Galleria ou MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter. In mammalian host cells, a number of viral-based expression systems may be utilized. The isolated polynucleotides according to this invention are useful for detection of expression of $\sigma_{1\beta}$ genes in normal and tumor tissues. Therefore, in yet another aspect, the present invention relates to an assay for determining the amount of $\sigma_{1\beta}$ mRNA in a biological sample comprising the steps of: i) contacting that biological sample with a nucleic acid isolate consisting essentially of a nucleotide sequence that encodes $\sigma_{1\beta}$ or a unique portion thereof under conditions such that a nucleic acid:RNA hybrid molecule, such as a DNA:RNA hybrid molecule, can be formed; and ii) determining the amount of hybrid molecule present, the amount of hybrid molecule indicating the amount of $\sigma_{1\beta}$ mRNA in the sample.

One particular embodiment of this aspect of this invention comprises a cell, preferably a mammalian cell, transformed with a DNA of the invention, wherein the transforming DNA is capable of being expressed to produce the functional polypeptide of an $\sigma_{1\beta}$ gene. For long-term, high-yield production of recombinant proteins, stable expression is preferred. For example, cell lines which stably express $\sigma_{1\beta}$ may be transformed using expression vectors which may contain viral origins of replication and/or endogenous expression elements and a selectable marker gene on the same or on a separate vector.

Host cells transformed with nucleotide sequences encoding $\sigma_{1\beta}$ may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode $\sigma_{1\beta}$ may be designed to contain signal sequences which direct secretion of $\sigma_{1\beta}$ through a prokaryotic or eukaryotic cell membrane. Other constructions may be used to join sequences encoding $\sigma_{1\beta}$ to nucleotide sequence encoding a polypeptide domain which will facilitate purification of soluble proteins, which are known in the art.

The presence of polynucleotide sequences encoding $\sigma_{1\beta}$ can be detected by DNA-DNA or DNA-RNA hybridization or amplification using probes or fragments or fragments of polynucleotides encoding $\sigma_{1\beta}$ and/or $\sigma_{1\beta}$. Nucleic acid amplification based assays involve the use of oligonucleotides or oligomers based on the sequences encoding $\sigma_{1\beta}$ to detect transformants containing DNA or RNA encoding $\sigma_{1\beta}$. A wide variety of labels and conjugation techniques are known by those skilled in the art and may be used in various nucleic acid and amino acid assays. Means for producing labeled hybridization or PCR probes for detecting sequences related to polynucleotides encoding $\sigma_{1\beta}$ include oligolabeling, nick translation, end-labeling or PCR amplification using a labeled nucleotide. Alternatively, the sequences encoding $\sigma_{1\beta}$, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

As noted above, the present invention provides isolated and purified $\sigma_{1\beta}$ proteins, such as mammalian (or more preferably human) $\sigma_{1\beta}$. Such proteins can be purified from host cells which express the same, in accordance with known techniques, or even manufactured synthetically. Nucleic acids of the present invention, constructs containing the same and host cells that express the encoded proteins are useful for making proteins of the present invention.

Proteins of the present invention are useful as immunogens for making antibodies as described herein, and these antibodies and proteins provide a "specific binding pair." Such specific binding pairs are useful as components of a variety of immunoassays and purification techniques, as is known in the art.

Fragments of the proteins encoded by SEQ ID NOS: 2 and 4 are expressly encompassed by the present invention. A fragment is a sub-sequence of contiguous amino acids that shares sequence with the full-length protein but is shorter than the full-length protein or polypeptide. The fragment according to the present invention will either retain the functionality or activity of the full length protein, or will comprise an antigenic site (i.e., an epitope) that may be used to raise antibodies that bind the full length protein. For example, a fragment of a protein of SEQ ID NO: 2 or 4 may exhibit $\sigma_2$-like binding activity, as defined herein. A fragment of the present invention may bind $\sigma_{1\beta}$ specific ligands, as provided herein. A fragment may be as short as three amino acids, or five amino acids, but is preferably longer than about ten amino acids. A fragment of the proteins of the present invention may be as long as 15 amino acids, or as long as 20 amino acids, or 25 amino acids, or even longer.

In general, those skilled in the art will appreciate that minor deletions or substitutions may be made to the amino acid sequences of peptides of the present invention without unduly adversely affecting the activity thereof. Thus, proteins and peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydrophobicity/ hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or lie; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gin, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gin or Ser, preferably Gln; KGln may be replaced with His, Lys, Glu, Asn, or Ser, preferably Asn or Ser; Ser may be replaced with Gln, Thr, Pro, Cys or Ala; Thr may be replaced with Gin or Ser, preferably Ser; Lys may be replaced with Gin or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function with enzymes.

A variety of protocols for detecting and measuring the expression of $\sigma_{1\beta}$ using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on $\sigma_{1\beta}$ is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; *J. Exp. Med.* 158:1211–1216).

In addition to recombinant production, fragments of $\sigma_{1\beta}$ may be produced by direct peptide synthesis using solid-phase techniques (Merrifield J. (1963) *J. Am. Chem. Soc.* 85, 2149–2154). Protein synthesis may be performed using manual techniques or by automation. Automated synthesis may be achieved, for example, using Applied Biosystems 431A Peptide Synthesizer (Perkin Elmer). Various fragments of $\sigma_{1\beta}$ may be chemically synthesized separately and combined using chemical methods to produce the full length molecule.

Antibodies that specifically bind to the proteins of the present invention (i.e., antibodies which bind to a single antigenic site or epitope on the proteins) are useful for a variety of diagnostic and imaging purposes.

Antibodies to $\sigma_{1\beta}$ may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with $\sigma_{1\beta}$ or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to $\sigma_{1\beta}$ have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of $\sigma_{1\beta}$ amino acids may be fused with those of another protein such as keyhole limpet hemocyanin and antibody produced against the chimeric molecule.

Monoclonal antibodies to $\sigma_{1\beta}$ may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, G. et al. (1975) *Nature*, 256, 495–497; Kozbor, D. et al. (1985) *J. Immunol. Methods* 81, 31–42; Cote, R. J. et al. (1983) *Proc. Natl. Acad. Sci. USA* 80, 2026–2030; Cole, S. P. et al. (1984) *Mol. Cell Biol.* 62, 109–120.

In addition, techniques developed for the production of "chimeric antibodies", the splicing of mouse antibody genes to human antibody genes to obtain a molecule with appropriate antigen specificity and biological activity can be used (Morrison, S. L. et al. (1984) *Proc. Natl. Acad. Sci.* 81, 6851–6855; Neuberger, M. S. et al. (1984) *Nature* 312: 604–608; Takeda, S. et al. (1985) *Nature* 314:452–454). Alternatively, techniques described for the production of single chain antibodies may be adapted, using methods known in the art, to produce $\sigma_{1\beta}$-specific single chain antibodies. Antibodies with related specificity, but of distinct idiotypic composition, may be generated by chain shuffling from random combinatorial immunoglobin libraries (Burton D. R. (1991) *Proc. Natl. Acad. Sci.* 88, 11120-3).

Antibodies may also be produced by inducing in vivo production in the lymphocyte population or by screening immunoglobulin libraries or panels of highly specific binding reagents as disclosed in the literature. See, e.g., Orlandi, R. et al. (1989) *Proc. Natl. Acad. Sci*, 86, 3833–3837; Winter, G. et al. (1991) *Nature* 349,:293–299.

Antibody fragments which contain specific binding sites for $\sigma_{1\beta}$ may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity. See Huse, W. D. et al. (1989) *Science* 254, 1275–1281.

The antibody can be labeled with a detectable moiety or attached to a solid support by methods known in the art to facilitate detection of an antibody/antigen complex. Such a detectable moiety will allow visual detection of a precipitate or a color change, visual detection by microscopy, or automated detection by spectrometry or radiometric measurement or the like. Examples of detectable moieties include fluorescein and rhodamine (for fluorescence microscopy), horseradish peroxidase (for either light microscopy or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, *Antibodies: A Laboratory Manual*, Cold Spring Harbor Laboratory, Cold Spring Harbor, N.Y., 1988).

Thus, by following the teachings of the present disclosure, including application of generally known immunological methods cited herein, one of ordinary skill in the art is able to obtain $\sigma_{1\beta}$-specific antibodies and use them in a variety of immunological assays, for example, for diagnostic detection of unusually high or low expression in normal or tumor tissues. Thus, the present invention also relates to a bioassay for detecting an $\sigma_{1\beta}$ antigen in a biological sample comprising the steps of: i) contacting that sample with an antibody of the present invention specific for an $\sigma_{1\beta}$ polypeptide, under conditions such that a specific complex of that antibody and that antigen can be formed; and ii) determining the amount of that antibody present in the form of those complexes.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between $\sigma_{1\beta}$ and its specific antibody. A two-site, monoclonal-based immunoassay utilizing monoclonal antibodies reactive to two non-interfering $\sigma_{1\beta}$ epitopes is preferred, but a competitive binding assay may also be employed.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Assays for detecting the polynucleotides encoding $\sigma_{1\beta}$ in a cell, or the extent of amplification thereof, typically involve, first, contacting the cells or extracts of the cells containing nucleic acids therefrom with an oligonucleotide that specifically binds to $\sigma_{1\beta}$ polynucleotide as given herein (typically under conditions that permit access of the oligonucleotide to intracellular material), and then detecting the presence or absence of binding of the oligonucleotide thereto. Again, any suitable assay format may be employed (see, e.g., U.S. Pat. No. 4,358,535 to Falkow et al.; U.S. Pat. No. 4,302,204 to Wahl et al.; U.S. Pat. No. 4,994,373 to Stavrianopoulos et al; U.S. Pat. No. 4,486,539 to Ranki et al.; U.S. Pat. No. 4,563,419 to Ranki et al.; and U.S. Pat. No. 4,868,104 to Kurn et al.) (the disclosures of which applicant specifically intends be incorporated herein by reference).

In a preferred embodiment, the $\sigma_{1\beta}$ proteins, nucleic acids, variants, modified proteins, and cells containing the $\sigma_{1\beta}$ nucleic acids or proteins are used in screening assays to identify ligands specific for the $\sigma_{1\beta}$ receptor. Identification of $\sigma_{1\beta}$ receptor ligands permits the design of tumor imaging, diagnostic and treatment methods.

The ability of a $\sigma$ receptor to bind [$^3$H](+)pentazocine is termed $\sigma_1$-like binding. [$^3$H]DTG has about the same affinity for $\sigma_1$ and $\sigma_2$ receptors. Thus, the binding of [$^3$H]DTG in the presence of pentazocine to mask the $\sigma_1$ is defined as $\sigma_2$-like binding. As used herein, the term "$\sigma_{1\beta}$ ligand" comprises any compound that is capable of binding to $\sigma_{1\beta}$ receptors to a measurable degree. Preferably, the compound binds selectively to $\sigma_{1\beta}$ receptors as compared to other sigma receptors, including $\sigma_1$ and $\sigma_2$. A compound's ability to bind to $\sigma_{1\beta}$ receptors can be determined using binding assays that are known in the art or can be determined using binding assays similar to those described herein. Preferred $\sigma_{1\beta}$ ligands bind at least 2, at least 3, at least 5, at least 10, or at least 25 times more readily to a $\sigma_{1\beta}$ receptor than to another sigma receptor.

The assays described herein preferably utilize the human $\sigma_{1\beta}$ or rodent $\sigma_{1\beta}$ (mice, rats, hamsters, guinea pigs, etc.), although $\sigma_{1\beta}$ of other mammalian proteins may also be used, including livestock/farm animals (cows, sheep, pigs, horses, etc.) and primates. These latter embodiments may be preferred in the development of animal models of human disease. In some embodiments, as outlined herein, variant or derivative $\sigma_{1\beta}$ proteins may be used, including deletion $\sigma_{1\beta}$ proteins and protein fragments, as outlined above.

In a preferred embodiment, the methods comprise combining a $\sigma_{1\beta}$ protein and a candidate compound, and determining the binding of the candidate compound to the $\sigma_{1\beta}$ proteins. In other embodiments, further discussed below, binding interference is determined.

The term "candidate compound" as used herein describes any molecule, e.g., protein, small organic molecule, carbohydrates (including polysaccharides), polynucleotide, lipids, etc. Generally a plurality of assay mixtures are run in parallel with different compound concentrations to obtain a differential response to the various concentrations. Typically, one of these concentrations serves as a negative control, i.e., at zero concentration or below the level of detection. In addition, positive controls, i.e. the use of compounds known to alter $\sigma_{1\beta}$ activity, may be used.

Candidate compounds encompass numerous chemical classes, though typically they are organic molecules, preferably small organic compounds having a molecular weight of more than 100 and less than about 2,500 daltons. Candidate compounds comprise functional groups necessary for structural interaction with proteins, particularly hydrogen bonding, and typically include at least an amine, carbonyl, hydroxyl or carboxyl group, preferably at least two of the functional chemical groups. The candidate compounds often comprise cyclical carbon or heterocyclic structures and/or aromatic or polyaromatic structures substituted with one or more of the above functional groups. Candidate compounds are also found among biomolecules including peptides, saccharides, fatty acids, steroids, purines, pyrimidines, derivatives, structural analogs or combinations thereof.

Candidate compounds are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological compounds may be subjected to directed or random chemical modifications, such as acylation, alkylation, esterification, amidification to produce structural analogs.

In a preferred embodiment, a library of different candidate compounds are used. Preferably, the library should provide a sufficiently structurally diverse population of randomized compounds to effect a probabilistically sufficient range of diversity to allow binding to a particular target. Accordingly, an interaction library should be large enough so that at least one of its members will have a structure that gives it affinity for the target.

Generally, in a preferred embodiment of the methods herein, for example for binding assays, the $\sigma_{1\beta}$ proteins or the candidate compound is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, TEFLON®, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block important sites on the protein when the protein is bound to the support), direct binding to "sticky" or ionic supports, chemical crosslinking, the synthesis of the protein or compound on the surface, etc. Following binding of the protein or compound, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the $\sigma_{1\beta}$ proteins is bound to the support, and a candidate compound is added to the assay. Alternatively, the candidate compound is bound to the support and the $\sigma_{1\beta}$ proteins is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays, and the like.

The determination of the binding of the candidate compound to the $\sigma_{1\beta}$ proteins may be done in a number of ways. In a preferred embodiment, the candidate bioactive compound is labeled, and binding determined directly. For example, this may be done by attaching all or a portion of the $\sigma_{1\beta}$ proteins to a solid support, adding a labeled candidate compound (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures. The label can directly or indirectly provide a detectable signal.

In some embodiments, only one of the components is labeled. For example, the proteins (or proteinaceous candidate compounds) may be labeled at tyrosine positions using $^{125}$I, or with fluorophores. Alternatively, more than one component may be labeled with different labels; using $^{125}$I for the proteins, for example, and a fluorophor for the candidate compounds.

In a preferred embodiment, the binding of the candidate bioactive compound is determined through the use of competitive binding assays. In this embodiment, the competitor is a binding moiety known to bind to the target molecule (i.e. $\sigma_{1\beta}$ proteins), such as an antibody, peptide, binding partner, ligand, etc. In a preferred embodiment, the competitor is a cullin. Under certain circumstances, there may be competitive binding as between the candidate compound and the binding moiety, with the binding moiety displacing the candidate compound. This assay can be used to determine candidate compounds which interfere with binding between $\sigma_{1\beta}$ proteins and its biological binding partners. "Interference of binding" as used herein means that native binding of the $\sigma_{1\beta}$ proteins differs in the presence of the candidate compound. The binding can be eliminated or can be with a reduced affinity. Therefore, in one embodiment, interference is caused by, for example, a conformation change, rather than direct competition for the native binding site.

In one embodiment, the candidate compound is labeled. Either the candidate compound, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate compound. Displacement of the competitor is an indication that the candidate compound is binding to the $\sigma_{1\beta}$ proteins and thus is capable of binding to, and potentially modulating, the activity of the $\sigma_{1\beta}$ proteins. In this embodiment, either component can be labeled. Thus, for example, if the competitor is labeled, the presence of label in the wash solution indicates displacement by the compound. Alternatively, if the candidate compound is labeled, the presence of the label on the support indicates displacement.

In an alternative embodiment, the candidate compound is added first, with incubation and washing, followed by the competitor. The absence of binding by the competitor may indicate that the candidate compound is bound to the $\sigma_{1\beta}$ proteins with a higher affinity. Thus, if the candidate compound is labeled, the presence of the label on the support, coupled with a lack of competitor binding, may indicate that the candidate compound is capable of binding to the $\sigma_{1\beta}$ proteins.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In this way, ligands for the $\sigma_{1\beta}$ receptor are identified. Ligands useful for diagnostic or pharmacological applications are include those compounds that are able to enhance or interfere with the activity of the $\sigma_{1\beta}$ proteins.

The present invention further provides a method for diagnostic imaging of a mammalian tissue which has cell surface $\sigma_{1\beta}$ receptors which includes administering to a mammal a diagnostic imaging amount of a compound of the present invention and detecting an image of a tissue having an abundance of cells with $\sigma_{1\beta}$ receptors. Suitable subjects are preferably human subjects, but may also be other mammalian subjects, such as rodents, primates, dogs, cats and livestock (i.e., for veterinary or animal modeling purposes). Imaging cells that have cell surface $\sigma_{1\beta}$ receptors may occur in vivo or in vitro, with in vitro methods being presently preferred.

According to the present invention a method for detecting a mammalian tumor or a tissue containing cell surface $\sigma_{1\beta}$ receptor includes administering to a subject a composition including a diagnostic imaging amount of at least ligand for the $\sigma_{1\beta}$ receptor. Preferably the ligand is detectably labeled (i.e., labeled in such a way that the presence of the ligand, particularly the ligand binding to the receptor, can be detected by means described herein). Such a diagnostic imaging amount is a dosage of at least one of the subject compounds which permits sufficient tumor or tissue localization of the ligand to allow detection of the tumor or tissue.

As described herein a tumor or tissue labeled with one or more of the present compounds can be detected using a radiation detector, e.g. a gamma-radiation detector. One such procedure utilizes scintography (scintillation counter). Tomographic imaging procedures such as single photon emission computed tomography (SPECT) or positron emission tomography (PET) can also be used to improve visualization.

In another embodiment the present invention provides a method for in vitro detection of a cancer cell in a mammalian tissue sample which includes contacting a mammalian tissue sample with an in vitro diagnostic imaging amount of a diagnostic compound for a time and under conditions sufficient for binding of the compound to a $\sigma_{1\beta}$ receptors on the cancer cell and detecting such binding.

Samples can be collected by procedures known to the skilled artisan, e.g. by collecting a tissue biopsy or a body fluid, by aspirating for tracheal or pulmonary samples and the like.

As used herein any mammalian tissue can be tested in vitro. Preferred tissues for in vitro testing include lung, bronchial, lymph, skin, brain, liver, prostate, breast, any tumor of neural origin and the like. Samples can be sectioned, e.g. with a microtome, to facilitate microscopic examination and observation of bound compound. Samples can also be fixed with an appropriate fixative either before or after incubation with one of the present compounds to improve the histological quality of sample tissues.

For detection, of cellular binding of one of $\sigma_{1\beta}$-specific ligand, samples can be incubated in the presence of a selected compound, then washed and counted in a standard scintillation counter. Alternatively, samples can be dipped in photoemulsion and the signal detected under light microscopy after several days, as exposed silver grains.

Ligands of $\sigma_{1\beta}$ can be labeled using any of a number of techniques which are well known in the art. For example, a radioisotope can be incorporated into said compound or appended to ligands using techniques well known in the art, for example, techniques analogous to those described in Arthur Murry III, D. Lloyd Williams; *Organic Synthesis with Isotopes*, vol. I and II, Interscience Publishers Inc., N.Y. (1958) and Melvin Calvin et al. *Isotopic Carbon*, John Wiley and Sons Inc., N.Y. (1949).

Any radioisotope capable of being detected in a diagnostic procedure can be employed as a label. For example, suitable radioisotopes include: carbon-11, fluorine-18, fluorine-19, iodine-123 and iodine-125. Preferably, $\sigma_{1\beta}$ ligands are labeled by appending one or more radioisotopes of a halogen (e.g., iodine-123) to an aromatic ring.

Additionally, $\sigma_{1\beta}$ ligands can be labeled with a metal chelating group optionally comprising a radionuclide, such as a metallic radioisotope. Such chelating groups are well known in the art and include polycarboxylic acids such as, for example, diethylenetriaminepentaacetic acid, ethylenediaminetetraacetic acid, and the like, or analogs or homologs thereof, as well as the chelating groups disclosed in S. Meegalla et al. *J. Am. Chem. Soc.* 117 11037–11038, 1995 and in S. Meegalla et al. *Bioconjugate Chem.* 7:421–429, 1996. The chelating group or the radionuclide therein may be attached directly to a ligand, by means of a divalent or bifunctional organic linker group. Such bifunctional linker groups are well known in the art and are preferably less than about 50 angstroms in length. Examples of suitable linker groups include 2-aminoethyl, 2-mercaptoethyl, 2-aminopropyl, 2-mercaptopropyl, e-amino caproic acid, 1,4-diaminobutane, and the like.

Any metallic radioisotope capable of being detected in a diagnostic procedure can be employed as a radionuclide. For example, suitable radioisotopes include: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-56, Cobalt-57, Cobalt-58, Cobalt-60, Cobalt-64, Erbium-169, Europium-152, Gadolinium-153, Gold 195, Gold 199, Hafnium-175, Hafnium-175–181, Indium-111, Iridium-192, Iron-55, Iron-59, Krypton-85, Lead-210, manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. Iodine-123 and technetium-99m may be particularly useful for SPECT imaging studies, and rhenium-186 and Yttrium-90 may be particularly useful for radiation therapy.

Any suitable imaging technique or diagnostic procedures that can be used to determine the extent to which a $\sigma_{1\beta}$ ligand binds to tumor cells can be used in conjunction with the methods of the invention. Suitable nuclear medicine imaging techniques include Single Photon Emission Computed Tomography (SPECT), Positron Emission Tomography (PET), Planar scintigraphy, and magnetic resonance imaging (see E. Bombardieri, et al. *Eur. J. Nuc. Med.*, 1997, 24, 809–824). Preferred imaging techniques include SPECT and PET, which can image and provide information about an entire tumor.

The $\sigma_{1\beta}$ receptor exhibits $\sigma_2$-like binding, as described in experimental detail below. As such, methods for determining the proliferative state of a cell by determining the cell's ability to bind $\sigma_2$ receptors may now be carried out using a cell's ability to bind $\sigma_{1\beta}$. These methods are described in international patent applications PCTUS97/04403 (claiming priority from U.S. Provisional Application No. 60/013,717) and PCT/US00/13834 (claiming priority from U.S. Provisional Application No. 60/135,274), and in Wheeler et al., *Br. J. Cancer* 86, 1223–1234 (2000), all of which are hereby incorporated in their entirety.

Briefly, these methods of determining the proliferative status of cancer cells are carried out by determining the ability of proliferative cells to bind $\sigma_1$ and $\sigma_{1\beta}$ ligands, respectively. The ratio of $\sigma_{1\beta}$ to $\sigma_1$ density on a cell is an indicator of the proliferative state of the cell. In one embodiment, the methods are carried out by contacting the cells with a detectably labeled $\sigma_1$ receptor ligand and a detectably labeled $\sigma_{1\beta}$ receptor ligand, and determining the extent to which the ligands bind to the cells, wherein the extent provides a measure of the proliferative status of the cell. In other words, the method may be carried out by determining the density of $\sigma_1$ receptors and $\sigma_{1\beta}$ receptors of the cell, wherein density is measured by the amount of binding of $\sigma_1$ receptor ligands to $\sigma_{1\beta}$ receptors and the amount of binding of $\sigma_{1\beta}$ receptor ligands to $\sigma_{1\beta}$ receptors. The respective densities of $\sigma_{1\beta}$ receptors to the density of $\sigma_1$ receptors of the cell, are indicative of the proliferative status of the cell, wherein a higher density of $\sigma_{1\beta}$ receptors as compared to $\sigma_1$ receptors indicates that the cancer cells are in a proliferative state. In particular, a ratio of density of $\sigma_{1\beta}$ receptor binding to density of $\sigma_1$ binding greater than about 1.5 or 2, or preferably greater than about 3, or even more preferably greater than about 5, and most preferably greater than about eight or ten, indicates that the cell is in a proliferative state. Alternatively, the $\sigma_2$-like binding of $\sigma_{1\beta}$ receptors of, for example, tumor cells may be determined and then compared to the same measurement of the tumor cells taken at an earlier time. An increase in the amount of $\sigma_2$-like binding over the first or earlier measurement may indicate that the tumor has shifted to a more proliferative status.

Pharmaceutical formulations of the present invention comprise ligands for the $\sigma_{1\beta}$ receptor that are bound to compounds with pharmacological activity (i.e., anticancer therapy) in a pharmaceutically acceptable carrier. Other embodiments of the invention comprise ligands for the $\sigma_{1\beta}$ receptor that are bound to detectable labels (i.e., fluorophores, chromophores, radioactive compounds) in a pharmaceutically acceptable carrier. Suitable pharmaceutical formulations include those suitable for inhalation, oral, rectal, topical, (including buccal, sublingual, dermal, vaginal and intraocular), parenteral (including subcutaneous, intradermal, intramuscular, intravenous and intraarticular) and transdermal administration. The compositions may conveniently be presented in unit dosage form and may be prepared by any of the methods well known in the art. The most suitable route of administration in any given case may depend upon the anatomic location of the condition being treated in the subject, the nature and severity of the condition being treated, and the particular pharmacologically active compound which is being used. The formulations may conveniently be presented in unit dosage form and may be prepared by any of the methods well known in the art.

In the manufacture of a medicament according to the invention (the "formulation"), pharmacologically active compounds or the physiologically acceptable salts thereof (the "active compounds") are typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 99% by weight of the active compound. One or more active compounds may be incorporated in the formulations of the invention, which formulations may be prepared by any of the well known techniques of pharmacy consisting essentially of admixing the components, optionally including one or more accessory therapeutic ingredients.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the pharmaceutically active compounds identified with the methods described herein may be lyophilized to produce a lyophilizate which may be reconstituted with a pharmaceutically acceptable carrier, such as water, to regenerate a liposomal suspension.

In addition to the pharmacologically active compounds, the pharmaceutical formulations may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical formulations of the present invention may be lyophilized using techniques well known in the art.

Useful dosages of the detectably labeled $\sigma_{1\beta}$ ligands can be determined by comparing their in vitro activity, and in vivo activity in animal models. Methods for the extrapolation of effective dosages in mice, and other animals, to humans are known to the art; for example, see U.S. Pat. No. 4,938,949. Generally, the concentration of the compound(s) in a liquid composition, such as a lotion, will be from about 0.1–25 wt- %, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

The following Examples are provided to illustrate the present invention, and should not be construed as limiting thereof.

EXAMPLE 1

Overview of Methods and Results

Using reverse-transcriptase-polymerase chain (RT-PCR) with flanking σ1-specific primers, the present inventors identified a novel variant in 67 mouse mammary adenocarcinoma cells and in human MCF-breast tumor cells. The cDNA of the variant encodes a 193 amino acid residue protein that is identical to the sequence of the mouse $\sigma_1$ receptor with the exception of a 90 base-pair in-frame deletion positioned about 18 base pairs downstream of the transmembrane domain. Although the inventors do not wish to be bound to any particular theory of the invention, this deletion occurs at the border of exon 2 and exon 3 and may therefore arise from alternative splicing.

The splice variant, herein referred to as the receptor $\sigma_{1B}$, was cloned into the expression vector pCDNA3 and transfected into COS-1 cells using LIPOFECTAMINE™. Expression of $\sigma_{1\beta}$ was assessed by binding to either [$^3$H] (+)-pentazocine (σ1-like binding) or [$^3$H]DTG plus cold pentazocine ($\sigma_2$-like binding). The $\sigma_{1\beta}$ receptor was found to have almost no $\sigma_1$ activity; however, the $\sigma_2$-like binding activity was increased by four-fold relative to empty vector controls. The tissue distribution of $\sigma_{1\beta}$ was assessed by the RT-PCR technique using RNA isolated from the tissues of normal C3H mice. A similar sized PCR product was detected in mouse brain, liver, heart, lung, spleen, intestine and kidney.

EXAMPLE 2

RT-PCR and Cloning of Novel Variant

Total RNA was isolated form 67 mouse and MCF-7 human breast cells. The following primers were used for RT-PCR using the GeneAmp

```
Upstream primer:   5'-GAACGAATTCAGAAGTCCGTGGGCCGCGGGA-3'  [SEQ ID NO: 5]

Downstream primer: 5'-TAACGGTACCTCAGGAGTCTTGGCCAAAGAG-3'  [SEQ ID NO: 6]
```

The RT-PCR products were separated on an agarose gel, shown in FIG. 1. The numbers to the left of the gel indicate number of base pairs (bp=base pairs); the lane marked "M" are size-markers; the lane labeled 67 is are the RT-PCR products isolated from the mouse cells; the lane marked MCF-7 indicates the RT-PCR products isolated from the human breast tumor cells. The 600 base-pair products were isolated from the agarose gels. The RT-PCR products were directionally cloned into the pCMV-5 vector. The products were then sequenced.

The mRNA sequence (cDNA sequence) of human $\sigma_{1\beta}$ was determined. The sequence has GenBank Accession Number AF226604 and is set forth in FIG. 2 and as follows:

```
SEQ ID NO: 1

ATGCAGTGGGCCGTGGGCCGGCGGTGGGCGTGGGCCGCGCTGCTC

CTGGCTGTCGCAGCGGTGCTGACCCAGGTCGTCTGGCTCTGGCTGG
```

-continued

```
GTACGCAGAGCTTCGTCTTCCAGCGCGAAGAGATAGCGCAGTTGGCG
CGGCAGTACGCTGGGCTGGACCACGAGCTGGCCTTCTCTCGTCTGAT
CGTGGAGCTGCGGCGGCTGCACCCAGGCCACGTGCTGCCCGACGAG
GAGCTGCAGTGGGTGTTCGTGAATGCGGGTGGCTGGATGGGCGCCA
TGTGCCTTCTGCACGCCTCGCTGTCCGAGTATGTGCTGCTCTTCGGC
ACCGCCTTGGGCTCCCGCGGCCACTCGGGGGAGACGGTAGTACACG
GGCCTGGTGAGGCAACAGCTGTGGAGTGGGGGCCAAACACATGGAT
GGTGGAGTACGGCCGGGGCGTCATCCCATCCACCCTGGCCTTCGCG
CTGGCCGACACTGTCTTCAGCACCCAGGACTTCCTCACCCTCTTCTAT
ACTCTTCGCTCCTATGCTCGGGGCCTCCGGCTTGAGCTCACCACCTA
CCTCTTTGGCCAGGACCCTTGA
```

The amino acid sequence of human $\sigma_{1\beta}$ [SEQ ID NO 2] is also set forth in FIG. 2, and is as follows [using single-letter amino acid code]:

```
M Q W A V G R R W A W A A L L L A V A A V L T Q V V W L W L G T Q S
F V F Q R E E I A Q L A R Q Y A G L D H E L A F S R L I V E L R R L H P
G H V L P D E E L Q W V F V N A G G W M G A M C L L H A S L S E Y V
L L F G T A L G S R G H S G E T V V H G P G E A T A V E W G P NT W M
V E Y G R G V I P S T L A F A L A D T V F S T Q D F L T L F Y T L R S Y
A R G L R L E L T T Y L F G Q D P *
```

FIG. 3 illustrates a comparison of the human $\sigma_1$ and $\sigma_{1\beta}$ receptor protein sequences.

The mRNA sequence (cDNA sequence) of mouse $\sigma_{1\beta}$ was determined. The sequence has GenBank Accession Number AF226604 and is set forth in FIG. 4 and as follows:

```
SEQ ID NO.4:
M P W A A G R R W A W I T L I L T I I A V L I Q A A W LW L G T Q N F V
F S R E E I A Q L A R Q Y AG L D H E L A F S R L I V E L R R L H PG H V
L P D E E L Q W V F V N A G G W M G A M C I L H A S L S E Y V L L F G
T A L G S H G H S G E T V V H G P G E A T A L E W G P N T W M V E Y
G R G V I P S T L F F A L A D T F F G T Q D Y L T L F Y T L R A Y A R G
L R L E L T T Y L F G Q D S *
```

SEQ ID NO: 3
```
ATGCCGTGGGCCGCGGGACGGCGGTGGGCATGGATCACCCTGATTC
TGACTATTATCGCAGTGCTGATCCAGGCCGCCTGGTTGTGGCTGGGC
ACTCAAAACTTCGTCTTCTCTAGAGAAGAAATAGCGCAGCTTGCTCGA
```

-continued
```
CAGTATGCGGGGCTGGACCATGAGCTTGCCTTCTCTCGGCTGATCGT
GGAGCTGCGGAGGCTGCACCCAGGCCACGTGCTGCCGGATGAGGAG
CTGCAGTGGGTATTTGTGAACGCGGGCGGCTGGATGGGCGCCATGT
GTATTCTGCACGCCTCGCTGTCTGAGTACGTGCTGCTCTTCGGCACC
GCCCTGGGCTCCCATGGCCATTCGGGAGAGACAGTTGTACACGGGC
CTGGAGAAGCAACGGCTCTGGAGTGGGGACCAAACACGTGGATGGT
GGAGTACGGCCGGGGTGTTATTCCGTCTACCCTGTTCTTTGCACTAG
CCGACACCTTCTTCGGCACCCAGGACTACCTCACACTCTTCTATACCC
TTCGGGCCTATGCCCGGGGCCTCCGGCTTGAGCTTACCACCTACCTC
TTTGGCCAAGACTCCTGA
```

The amino acid sequence of mouse $\sigma_{1\beta}$ [SEQ ID NO: 4] is also set forth in FIG. 4, and is as follows [using single-letter amino acid code]:

FIG. 5 is a comparison of the mouse $\sigma_1$ and $\sigma_{1\beta}$ receptor protein sequences.

EXAMPLE 3

Expression of the $\sigma_{1\beta}$ Receptor in COS-1 Cells

The 600 bp RT-PCR products of Example 2 were subcloned into pcDNA3 vectors. COS-1 cells were then transfected with either an empty pcDNA3 vector or the pcDNA3-cDNA construct using the LIPOFECTAMINE™ reagent.

EXAMPLE 4

Determination of the $\sigma_1$ Specific and $\sigma_2$-like Binding Activity Twenty four hours after transfection, the non-specific and $\sigma_1$ specific binding activity was determined by exposing the transfected COS-1 cells to [$^3$H](+)-pentazocine for 30 minutes at 25° C. For determination of $\sigma_2$-like binding activity, the cells were exposed to [$^3$H]DTG in the presence of 10 nM cold pentazocine, either with or without μM cold DTG, for 30 minutes at 25° C. Results of these experiments are provided in Table 1 and Table 2, below. Extent of binding is expressed in Bmax (fmol/mg protein).

TABLE 1

$\sigma_1$-like binding of $\sigma_{1\beta}$ receptor.

|  | Control | $\sigma_{1\beta}$ |
|---|---|---|
| Non-specific | 176 +/− 15 | 161 +/− 13 |
| Total binding | 881 +/− 14 | 1041 +/− 18 |
| Net [$^3$H]Pent | 705 | 880 |
| Ratio | 1.0 | 1.2 |

TABLE 2

$\sigma_2$ binding of $\sigma_{1\beta}$ Receptor.

|  | Control | $\sigma_{1\beta}$ |
|---|---|---|
| Non-specific | 1583 +/− 389 | 2535 +/− 478 |
| Total binding | 2598 +/− 654 | 6699 +/− 949 |
| Net [$^3$H]DTG | 1015 | 4164 |
| Ratio | 1.0 | 4.1 |

EXAMPLE 5

Distribution of the Receptor $\sigma 1\beta$ in Normal Tissue

Figure 6:
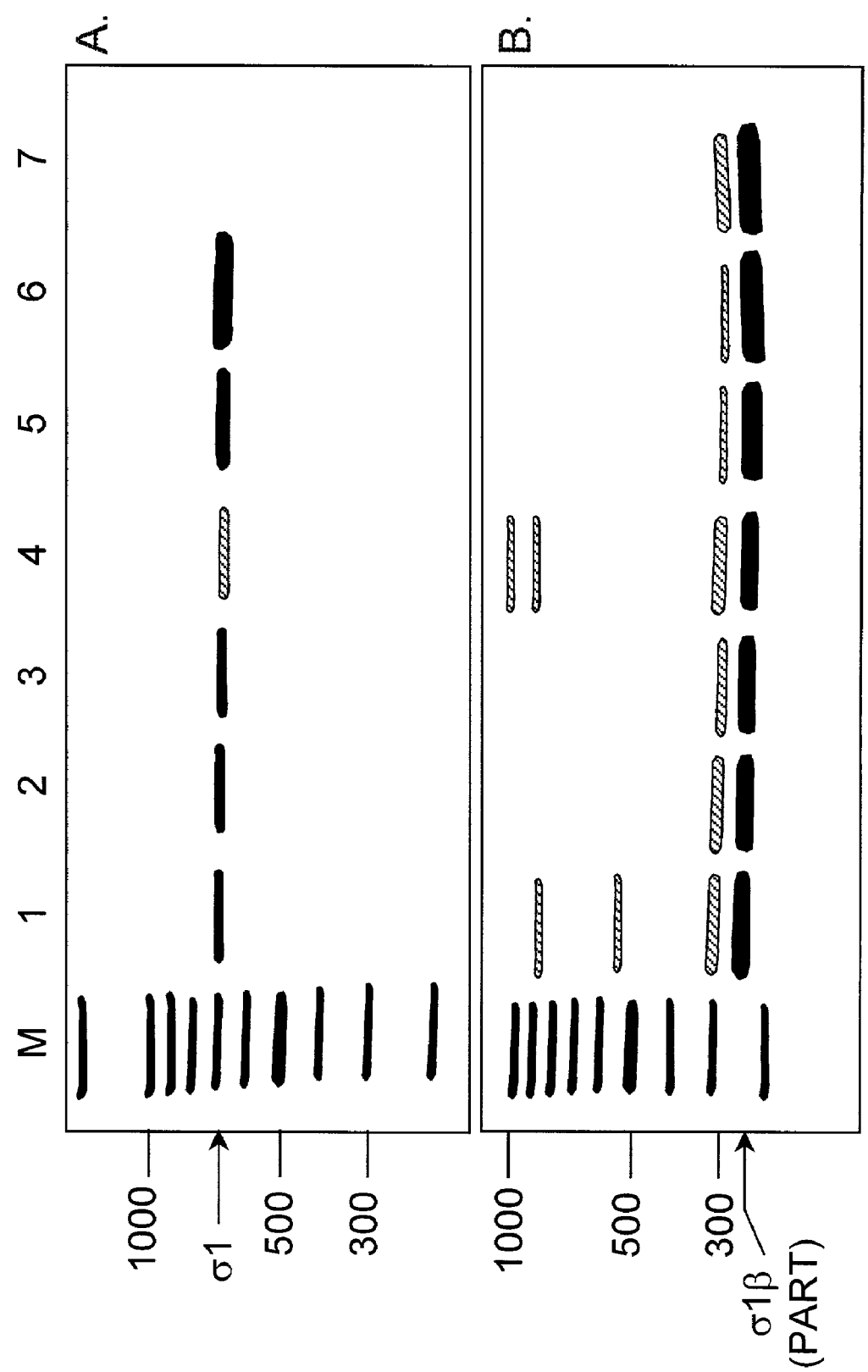
FIGS. 6A and 6B are photographic images of two gels illustrating the tissue distribution of the $\sigma_1$ receptor and the $\sigma_{1\beta}$ receptor.

The distribution in normal tissues of the $\sigma_{1\beta}$ receptor is shown in FIG. 6. FIG. 6A illustrates the gel run on RT-PCR compounds, using $\sigma_1$ specific primers. FIG. 6B illustrates the gel run on RT-PCR compounds, using $\sigma_{1\beta}$ specific primers. M indicates DNA size markers (length of product indicated to left of gels in number of base pairs); Lane 1 is product located in brain; Lane 2 is product located in heart; Lane 3 is product located in lung; Lane 4 is product located in spleen; Lane 5 is product located in kidney; Lane 6 is product located in liver; Lane 7 is product located in intestine.

EXAMPLE 6

Conclusion

Figure 7:
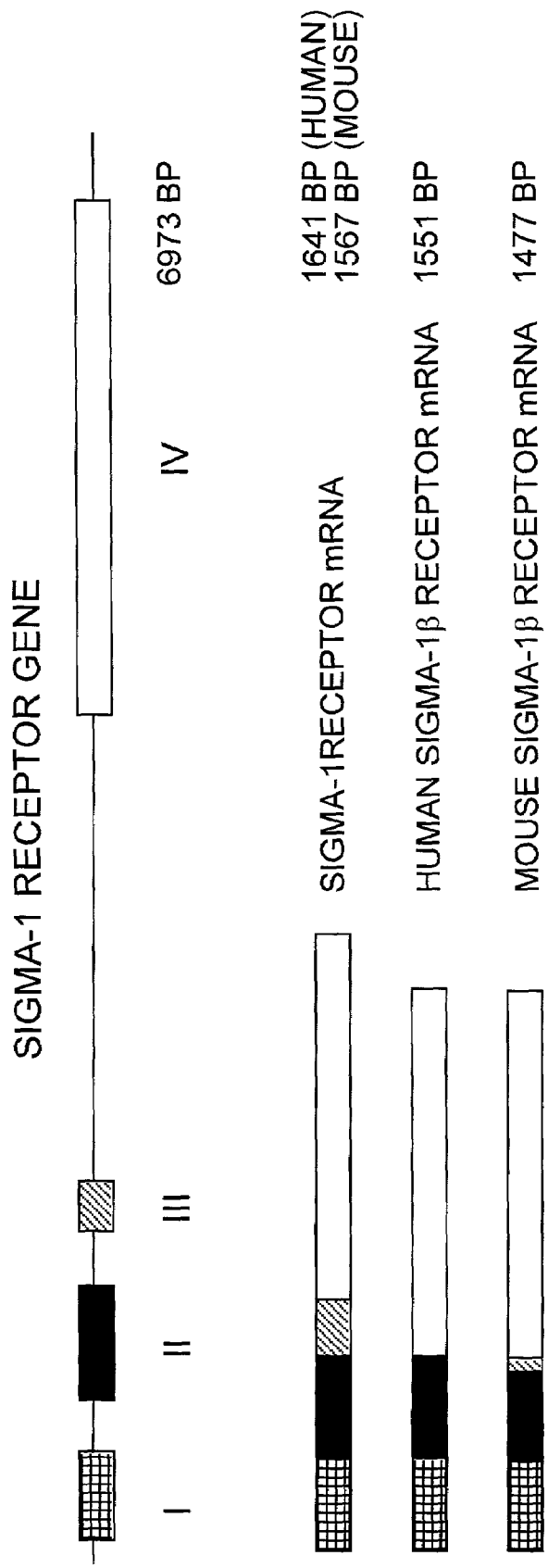
FIG. 7 is a schematic illustration of the sigma-1 ($\sigma_1$) receptor gene and the mRNAs of $\sigma_1$ receptor, human $\sigma_{1\beta}$ receptor, and mouse $\sigma_{1\beta}$ receptor. Exons I, II III and IV are indicated.

The $\sigma_{1\beta}$ receptor mRNA (cd region) was cloned from mouse and human breast cancer cells. When expressed in COS-1 cells, the $\sigma_{1\beta}$ receptor protein exhibits little to no $\sigma_1$ binding activity, but it does have strong $\sigma_2$ binding activity. The $\sigma_{1\beta}$ receptor appears to be widely distributed in normal tissues. A schematic illustration of the sigma-1 ($\sigma_1$) receptor gene and the mRNAs of $\sigma_1$ receptor, human $\sigma_{1\beta}$ receptor, and mouse $\sigma_{1\beta}$ receptors are set forth in FIG. 7. Exons I, II III and IV are indicated.

The foregoing is illustrative of the present invention and is not to be construed as limiting thereof. The invention is defined by the following claims, with equivalents of the claims to be included therein.

---

The invention claimed is:

1. An isolated polynucleotide which encodes for the amino acid sequence of SEQ ID NO: 2.

2. An isolated polynucleotide comprising the nucleotide sequence of SEQ ID NO:1.

3. An expression vector comprising a polynucleotide according to claim 1.

4. A An isolated cell comprising an expression vector according to claim 3.

5. An isolated cell comprising an expression vector according to claim 4 and capable of expressing $\sigma_{1\beta}$.

6. A An isolated transformed host cell comprising the polynucleotide of claim 1.

* * * * *

UNITED STATES PATENT AND TRADEMARK OFFICE
CERTIFICATE OF CORRECTION

| | | |
|---|---|---|
| PATENT NO. | : 7,049,425 B2 | Page 1 of 1 |
| APPLICATION NO. | : 09/823069 | |
| DATED | : May 23, 2006 | |
| INVENTOR(S) | : Wheeler et al. | |

It is certified that error appears in the above-identified patent and that said Letters Patent is hereby corrected as shown below:

Column 38,
Line 1 should read -- 4. An isolated cell comprising an expressin vector --

Line 5 should read -- 6. An isolated transformed host cell comprising the --

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 7,049,425 B2  Page 1 of 1
APPLICATION NO. : 09/823069
DATED : May 23, 2006
INVENTOR(S) : Wheeler et al.

It is certified that error appears in the above-identified patent and that said Letters Patent is hereby corrected as shown below:

Column 38,
Line 1 should read -- 4. An isolated cell comprising an expression vector --

Line 5 should read -- 6. An isolated transformed host cell comprising the --

This certificate supersedes Certificate of Correction issued September 19, 2006.

Signed and Sealed this

Thirtieth Day of January, 2007

JON W. DUDAS
*Director of the United States Patent and Trademark Office*

SEQUENCE LISTING

<160> NUMBER OF SEQ ID NOS: 8

<210> SEQ ID NO 1
<211> LENGTH: 579
<212> TYPE: DNA
<213> ORGANISM: Homo sapiens
<220> FEATURE:
<221> NAME/KEY: CDS
<222> LOCATION: (1)..(579)

<400> SEQUENCE: 1

```
atg cag tgg gcc gtg ggc cgg cgg tgg gcg tgg gcc gcg ctg ctc ctg      48
Met Gln Trp Ala Val Gly Arg Arg Trp Ala Trp Ala Ala Leu Leu Leu
1               5                   10                  15 gct gtc gca gcg gtg ctg acc cag gtc gtc tgg ctc tgg ctg ggt acg      96
Ala Val Ala Ala Val Leu Thr Gln Val Val Trp Leu Trp Leu Gly Thr
                20                  25                  30 cag agc ttc gtc ttc cag cgc gaa gag ata gcg cag ttg gcg cgg cag     144
Gln Ser Phe Val Phe Gln Arg Glu Glu Ile Ala Gln Leu Ala Arg Gln
            35                  40                  45 tac gct ggg ctg gac cac gag ctg gcc ttc tct cgt ctg atc gtg gag     192
Tyr Ala Gly Leu Asp His Glu Leu Ala Phe Ser Arg Leu Ile Val Glu
```

-continued

```
                   50                  55                  60
ctg cgg cgg ctg cac cca ggc cac gtg ctg ccc gac gag gag ctg cag      240
Leu Arg Arg Leu His Pro Gly His Val Leu Pro Asp Glu Glu Leu Gln
 65                  70                  75                  80 tgg gtg ttc gtg aat gcg ggt ggc tgg atg ggc gcc atg tgc ctt ctg      288
Trp Val Phe Val Asn Ala Gly Gly Trp Met Gly Ala Met Cys Leu Leu
                     85                  90                  95 cac gcc tcg ctg tcc gag tat gtg ctg ctc ttc ggc acc gcc ttg ggc      336
His Ala Ser Leu Ser Glu Tyr Val Leu Leu Phe Gly Thr Ala Leu Gly
                100                 105                 110 tcc cgc ggc cac tcg ggg gag acg gta gta cac ggg cct ggt gag gca      384
Ser Arg Gly His Ser Gly Glu Thr Val Val His Gly Pro Gly Glu Ala
            115                 120                 125 aca gct gtg gag tgg ggg cca aac aca tgg atg gtg gag tac ggc cgg      432
Thr Ala Val Glu Trp Gly Pro Asn Thr Trp Met Val Glu Tyr Gly Arg
        130                 135                 140 ggc gtc atc cca tcc acc ctg gcc ttc gcg ctg gcc gac act gtc ttc      480
Gly Val Ile Pro Ser Thr Leu Ala Phe Ala Leu Ala Asp Thr Val Phe
145                 150                 155                 160 agc acc cag gac ttc ctc acc ctc ttc tat act ctt cgc tcc tat gct      528
Ser Thr Gln Asp Phe Leu Thr Leu Phe Tyr Thr Leu Arg Ser Tyr Ala
                165                 170                 175 cgg ggc ctc cgg ctt gag ctc acc acc tac ctc ttt ggc cag gac cct      576
Arg Gly Leu Arg Leu Glu Leu Thr Thr Tyr Leu Phe Gly Gln Asp Pro
                180                 185                 190 tga                                                                  579
```

<210> SEQ ID NO 2
<211> LENGTH: 192
<212> TYPE: PRT
<213> ORGANISM: Homo sapiens

<400> SEQUENCE: 2

```
Met Gln Trp Ala Val Gly Arg Arg Trp Ala Trp Ala Ala Leu Leu Leu
 1               5                  10                  15

Ala Val Ala Ala Val Leu Thr Gln Val Val Trp Leu Trp Leu Gly Thr
                 20                  25                  30

Gln Ser Phe Val Phe Gln Arg Glu Glu Ile Ala Gln Leu Ala Arg Gln
             35                  40                  45

Tyr Ala Gly Leu Asp His Glu Leu Ala Phe Ser Arg Leu Ile Val Glu
         50                  55                  60

Leu Arg Arg Leu His Pro Gly His Val Leu Pro Asp Glu Glu Leu Gln
 65                  70                  75                  80

Trp Val Phe Val Asn Ala Gly Gly Trp Met Gly Ala Met Cys Leu Leu
                     85                  90                  95

His Ala Ser Leu Ser Glu Tyr Val Leu Leu Phe Gly Thr Ala Leu Gly
                100                 105                 110

Ser Arg Gly His Ser Gly Glu Thr Val Val His Gly Pro Gly Glu Ala
            115                 120                 125

Thr Ala Val Glu Trp Gly Pro Asn Thr Trp Met Val Glu Tyr Gly Arg
        130                 135                 140

Gly Val Ile Pro Ser Thr Leu Ala Phe Ala Leu Ala Asp Thr Val Phe
145                 150                 155                 160

Ser Thr Gln Asp Phe Leu Thr Leu Phe Tyr Thr Leu Arg Ser Tyr Ala
                165                 170                 175

Arg Gly Leu Arg Leu Glu Leu Thr Thr Tyr Leu Phe Gly Gln Asp Pro
                180                 185                 190
```

```
<210> SEQ ID NO 3
<211> LENGTH: 579
<212> TYPE: DNA
<213> ORGANISM: Mus musculus
<220> FEATURE:
<221> NAME/KEY: CDS
<222> LOCATION: (1)..(579)

<400> SEQUENCE: 3 atg ccg tgg gcc gcg gga cgg cgg tgg gca tgg atc acc ctg att ctg     48
Met Pro Trp Ala Ala Gly Arg Arg Trp Ala Trp Ile Thr Leu Ile Leu
1               5                   10                  15 act att atc gca gtg ctg atc cag gcc gcc tgg ttg tgg ctg ggc act     96
Thr Ile Ile Ala Val Leu Ile Gln Ala Ala Trp Leu Trp Leu Gly Thr
            20                  25                  30 caa aac ttc gtc ttc tct aga gaa gaa ata gcg cag ctt gct cga cag    144
Gln Asn Phe Val Phe Ser Arg Glu Glu Ile Ala Gln Leu Ala Arg Gln
        35                  40                  45 tat gcg ggg ctg gac cat gag ctt gcc ttc tct cgg ctg atc gtg gag    192
Tyr Ala Gly Leu Asp His Glu Leu Ala Phe Ser Arg Leu Ile Val Glu
    50                  55                  60 ctg cgg agg ctg cac cca ggc cac gtg ctg ccg gat gag gag ctg cag    240
Leu Arg Arg Leu His Pro Gly His Val Leu Pro Asp Glu Glu Leu Gln
65                  70                  75                  80 tgg gta ttt gtg aac gcg ggc ggc tgg atg ggc gcc atg tgt att ctg    288
Trp Val Phe Val Asn Ala Gly Gly Trp Met Gly Ala Met Cys Ile Leu
                85                  90                  95 cac gcc tcg ctg tct gag tac gtg ctg ctc ttc ggc acc gcc ctg ggc    336
His Ala Ser Leu Ser Glu Tyr Val Leu Leu Phe Gly Thr Ala Leu Gly
            100                 105                 110 tcc cat ggc cat tcg gga gag aca gtt gta cac ggg cct gga gaa gca    384
Ser His Gly His Ser Gly Glu Thr Val Val His Gly Pro Gly Glu Ala
        115                 120                 125 acg gct ctg gag tgg gga cca aac acg tgg atg gtg gag tac ggc cgg    432
Thr Ala Leu Glu Trp Gly Pro Asn Thr Trp Met Val Glu Tyr Gly Arg
    130                 135                 140 ggt gtt att ccg tct acc ctg ttc ttt gca cta gcc gac acc ttc ttc    480
Gly Val Ile Pro Ser Thr Leu Phe Phe Ala Leu Ala Asp Thr Phe Phe
145                 150                 155                 160 ggc acc cag gac tac ctc aca ctc ttc tat acc ctt cgg gcc tat gcc    528
Gly Thr Gln Asp Tyr Leu Thr Leu Phe Tyr Thr Leu Arg Ala Tyr Ala
                165                 170                 175 cgg ggc ctc cgg ctt gag ctt acc acc tac ctc ttt ggc caa gac tcc    576
Arg Gly Leu Arg Leu Glu Leu Thr Thr Tyr Leu Phe Gly Gln Asp Ser
            180                 185                 190 tga                                                                579

<210> SEQ ID NO 4
<211> LENGTH: 192
<212> TYPE: PRT
<213> ORGANISM: Mus musculus

<400> SEQUENCE: 4

Met Pro Trp Ala Ala Gly Arg Arg Trp Ala Trp Ile Thr Leu Ile Leu
1               5                   10                  15

Thr Ile Ile Ala Val Leu Ile Gln Ala Ala Trp Leu Trp Leu Gly Thr
            20                  25                  30

Gln Asn Phe Val Phe Ser Arg Glu Glu Ile Ala Gln Leu Ala Arg Gln
        35                  40                  45
```

```
Tyr Ala Gly Leu Asp His Glu Leu Ala Phe Ser Arg Leu Ile Val Glu
     50                  55                  60

Leu Arg Arg Leu His Pro Gly His Val Leu Pro Asp Glu Glu Leu Gln
 65                  70                  75                  80

Trp Val Phe Val Asn Ala Gly Gly Trp Met Gly Ala Met Cys Ile Leu
                 85                  90                  95

His Ala Ser Leu Ser Glu Tyr Val Leu Leu Phe Gly Thr Ala Leu Gly
            100                 105                 110

Ser His Gly His Ser Gly Glu Thr Val Val His Gly Pro Gly Glu Ala
        115                 120                 125

Thr Ala Leu Glu Trp Gly Pro Asn Thr Trp Met Val Glu Tyr Gly Arg
    130                 135                 140

Gly Val Ile Pro Ser Thr Leu Phe Phe Ala Leu Ala Asp Thr Phe Phe
145                 150                 155                 160

Gly Thr Gln Asp Tyr Leu Thr Leu Phe Tyr Thr Leu Arg Ala Tyr Ala
                165                 170                 175

Arg Gly Leu Arg Leu Glu Leu Thr Thr Tyr Leu Phe Gly Gln Asp Ser
            180                 185                 190
```

<210> SEQ ID NO 5
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 5
gaacgaattc agaagtccgt gggccgcggg a                                31

<210> SEQ ID NO 6
<211> LENGTH: 31
<212> TYPE: DNA
<213> ORGANISM: Artificial
<220> FEATURE:
<223> OTHER INFORMATION: Synthetic oligonucleotide primer

<400> SEQUENCE: 6
taacggtacc tcaggagtct tggccaaaga g                                31

<210> SEQ ID NO 7
<211> LENGTH: 223
<212> TYPE: PRT
<213> ORGANISM: Homo sapiens

<400> SEQUENCE: 7

```
Met Gln Trp Ala Val Gly Arg Arg Trp Ala Trp Ala Ala Leu Leu Leu
 1               5                  10                  15

Ala Val Ala Ala Val Leu Thr Gln Val Val Trp Leu Trp Leu Gly Thr
                 20                  25                  30

Gln Ser Phe Val Phe Gln Arg Glu Glu Ile Ala Gln Leu Ala Arg Gln
             35                  40                  45

Tyr Ala Gly Leu Asp His Glu Leu Ala Phe Ser Arg Leu Ile Val Glu
     50                  55                  60

Leu Arg Arg Leu His Pro Gly His Val Leu Pro Asp Glu Glu Leu Gln
 65                  70                  75                  80

Trp Val Phe Val Asn Ala Gly Gly Trp Met Gly Ala Met Cys Leu Leu
                 85                  90                  95

His Ala Ser Leu Ser Glu Tyr Val Leu Leu Phe Gly Thr Ala Leu Gly
            100                 105                 110
```

```
Ser Arg Gly His Ser Gly Arg Tyr Trp Ala Glu Ile Ser Asp Thr Ile
        115                 120                 125

Ile Ser Gly Thr Phe His Gln Trp Arg Glu Gly Thr Thr Lys Ser Glu
        130                 135                 140

Val Phe Tyr Pro Gly Glu Thr Val His Gly Pro Gly Glu Ala Thr
145                 150                 155                 160

Ala Val Glu Trp Gly Pro Asn Thr Trp Met Val Glu Tyr Gly Arg Gly
                165                 170                 175

Val Ile Pro Ser Thr Leu Ala Phe Ala Leu Ala Asp Thr Val Phe Ser
        180                 185                 190

Thr Gln Asp Phe Leu Thr Leu Phe Tyr Thr Leu Arg Ser Tyr Ala Arg
        195                 200                 205

Gly Leu Arg Leu Glu Leu Thr Thr Tyr Leu Phe Gly Gln Asp Pro
        210                 215                 220

<210> SEQ ID NO 8
<211> LENGTH: 223
<212> TYPE: PRT
<213> ORGANISM: Mus musculus

<400> SEQUENCE: 8

Met Pro Trp Ala Ala Gly Arg Arg Trp Ala Trp Ile Thr Leu Ile Leu
1               5                   10                  15

Thr Ile Ile Ala Val Leu Ile Gln Ala Ala Trp Leu Trp Leu Gly Thr
            20                  25                  30

Gln Asn Phe Val Phe Ser Arg Glu Glu Ile Ala Gln Leu Ala Arg Gln
        35                  40                  45

Tyr Ala Gly Leu Asp His Glu Leu Ala Phe Ser Arg Leu Ile Val Glu
    50                  55                  60

Leu Arg Arg Leu His Pro Gly His Val Leu Pro Asp Glu Glu Leu Gln
65                  70                  75                  80

Trp Val Phe Val Asn Ala Gly Gly Trp Met Gly Ala Met Cys Ile Leu
                85                  90                  95

His Ala Ser Leu Ser Glu Tyr Val Leu Leu Phe Gly Thr Ala Leu Gly
            100                 105                 110

Ser His Gly His Ser Gly Arg Tyr Trp Ala Glu Ile Ser Asp Thr Ile
        115                 120                 125

Ile Ser Gly Thr Phe His Gln Trp Lys Glu Gly Thr Thr Lys Ser Glu
        130                 135                 140

Val Phe Tyr Pro Gly Glu Thr Val His Gly Pro Gly Glu Ala Thr
145                 150                 155                 160

Ala Leu Glu Trp Gly Pro Asn Thr Trp Met Val Glu Tyr Gly Arg Gly
                165                 170                 175

Val Ile Pro Ser Thr Leu Phe Phe Ala Leu Ala Asp Thr Phe Phe Gly
        180                 185                 190

Thr Gln Asp Tyr Leu Thr Leu Phe Tyr Thr Leu Arg Ala Tyr Ala Arg
        195                 200                 205

Gly Leu Arg Leu Glu Leu Thr Thr Tyr Leu Phe Gly Gln Asp Ser
        210                 215                 220
```